(12) United States Patent
Nguyen-Dinh et al.

(10) Patent No.: US 11,190,113 B2
(45) Date of Patent: Nov. 30, 2021

(54) LEADLESS AUTONOMOUS CARDIAC CAPSULE WITH ROTATABLY-MOUNTED PIEZOELECTRIC ENERGY HARVESTER

(71) Applicant: CAIRDAC, Antony (FR)

(72) Inventors: An Nguyen-Dinh, La Riche (FR); Alaa Makdissi, Paris (FR); Willy Regnier, Longjumeau (FR)

(73) Assignee: CAIRDAC, Antony (FR)

( * ) Notice: Subject to any disclaimer, the term of this patent is extended or adjusted under 35 U.S.C. 154(b) by 548 days.

(21) Appl. No.: 16/270,561

(22) Filed: Feb. 7, 2019

(65) Prior Publication Data

US 2020/0259427 A1  Aug. 13, 2020

(51) Int. Cl.
*H02N 2/18* (2006.01)
*A61N 1/375* (2006.01)
*A61N 1/372* (2006.01)
*A61N 1/378* (2006.01)
*G05B 19/042* (2006.01)
*H01L 41/113* (2006.01)
*H02J 7/00* (2006.01)

(52) U.S. Cl.
CPC ........... *H02N 2/181* (2013.01); *A61N 1/3756* (2013.01); *A61N 1/3785* (2013.01); *A61N 1/37217* (2013.01); *A61N 1/37512* (2017.08); *A61N 1/37518* (2017.08); *G05B 19/042* (2013.01); *H01L 41/1134* (2013.01); *H02J 7/00* (2013.01); *H02N 2/183* (2013.01); *H02N 2/185* (2013.01); *G05B 2219/2639* (2013.01)

(58) Field of Classification Search
CPC ........ H02N 2/181; H02N 2/183; H02N 2/185; H01L 41/113; H01L 41/1134; A61N 1/37512; A61N 1/37518; A61N 1/37217; A61N 1/3756; A61N 1/3785; G05B 19/042; G05B 2219/2639
See application file for complete search history.

(56) References Cited

U.S. PATENT DOCUMENTS

| | | | |
|---|---|---|---|
| 7,812,466 B2 * | 10/2010 | Lu | H02N 2/188 290/1 R |
| 2011/0304240 A1 | 12/2011 | Meitav et al. | |
| 2013/0238073 A1 * | 9/2013 | Makdissi | A61N 1/36542 607/126 |
| 2015/0091415 A1 | 4/2015 | Deterre et al. | |
| 2018/0185638 A1 * | 7/2018 | Regnier | A61N 1/3785 |

* cited by examiner

*Primary Examiner* — Jaydi San Martin
(74) *Attorney, Agent, or Firm* — Steven M. Greenberg, Esq.; Shutts & Bowen LLP (57) ABSTRACT

An autonomous implantable capsule comprises a capsule body provided with an element for its anchoring to a patient's organ. An electronic unit is powered by an energy harvesting module provided with a pendular unit comprising an inertial mass coupled to an elastic piezoelectric beam forming a mechanical-electrical transducer for converting into electrical energy the oscillations of the beam. A mobile support, integral with the clamped end of the beam and mobile in axial rotation about the axis of the capsule body, can be directed by a controllable driver to adjust the angular position of the support so as to maximize the produced electrical power converted by the mechanical-electrical transducer.

15 Claims, 4 Drawing Sheets

LEADLESS AUTONOMOUS CARDIAC CAPSULE WITH ROTATABLY-MOUNTED PIEZOELECTRIC ENERGY HARVESTER

BACKGROUND OF THE INVENTION

Field of the Invention

The invention relates to autonomous medical devices, in particular the devices of the autonomous implantable capsule type, especially those devices which are intended to be implanted in a cardiac cavity.

Description of the Related Art

Recent advances in miniaturization of active devices and advances in life sciences allow from now on the development of a wide variety of fully autonomous, miniaturized implantable systems, for monitoring, diagnosis or treatment purposes. Such devices implement less invasive implantation procedures, provide more comfort, increased performances, and often open up access to new types of diagnoses and treatments.

The invention more particularly relates to those devices which incorporate a self-powering system comprising a mechanical energy harvesting device associated with an integrated energy storage component, such as a rechargeable battery or a high-performance capacitor.

Indeed, one of the critical aspects of these miniaturized devices is the power autonomy. The life duration of such an implant being about 8-10 years, given the very small dimensions it is not possible to use a conventional battery, even a high-density one.

The energy harvesting device, also known as "harvester" or "scavenger", addresses this drawback by collecting the mechanical energy resulting from the various movements undergone by the body of the implanted device. Those movements may have for origin a certain number of phenomena occurring for example at the rhythm of the heartbeats, such as periodic shakes of the wall on which the implant is anchored, the vibrations of the cardiac tissues linked i.a. to closings and openings of cardiac valves, or blood flow rate variations in the surrounding environment, which stress the implant and make it oscillate at the rhythm of the flow rate variations.

The mechanical energy collected by the harvester is converted into electrical energy (voltage or current), by means of a suitable mechanical-electrical transducer, for powering the various circuits and sensors of the device and for charging the energy storage component. This powering system allows the device to operate in full power autonomy during its whole life.

This energy harvesting technique is particularly well adapted for powering the implanted autonomous capsules having no physical connection with a remote device. These capsules are called for this reason "leadless capsules", for distinguishing them from the electrodes or sensors arranged at the distal end of a lead, through the whole length of which run one or several conductors connected to a generator connected to the opposite, proximal end.

The invention is nevertheless not limited to a particular type of capsule, nor to a leadless implant, and it is applicable as well to many other types of implantable medical devices, whatever the operational purpose thereof, cardiac or other.

In the cardiac application case, the leadless capsule continuously monitors the rhythm of the patient and if necessary issues to the heart electrical pulses for stimulation, resynchronization and/or defibrillation in case of rhythm disorders detected by the capsule. The leadless capsule may be an epicardial capsule, fixed to the outer wall of the heart, or an endocavitary capsule, fixed to the inner wall of a ventricular or atrial cavity, or a capsule fixed to the wall of a vessel near the myocardium. The fixation of the capsule to the implantation site is made through a protruding anchoring system extending the capsule body and designed to penetrate the cardiac tissue, in particular by means of a screw.

The capsule further comprises various electronic circuits, sensors, etc., as well as wireless communication emitter/receiver means for the remote exchange of data, the whole being integrated in a body of very small size that can be implanted at sites whose access is difficult or that leave little space available, such as the apex of the ventricle, the inner wall of the atrium, etc.

WO 2019/001829 A1 (Cairdac) describes an example of such a leadless intracardial capsule.

There exist several types of energy harvesters, based on different physical principles: system of the automatic wind-up watch movement type, mobile magnet system, bellows system or similar system collecting the blood pressure variations, etc.

The invention more particularly relates to the capsules or similar implantable devices whose energy harvester uses an inertial pendular unit subjected to the above-described external stresses.

An inertial pendular unit implements a transducer including in the capsule a mobile mass, called "seismic mass" or "inertial mass", which is driven according to the movements of the capsule, permanently subjected to the various external stresses described hereinabove. After each of these stresses, the inertial mass, which is coupled to an elastically deformable element, oscillates at a natural frequency of free oscillation.

The mechanical energy of the oscillation is converted into electrical energy by a mechanical-electrical transducer outputting an electrical signal. This signal is provided to a power management circuit of the capsule, which rectifies and regulates the electrical signal to output a stabilized direct voltage or current, for powering the various electronic circuits and sensors of the implant, as well as for charging the energy storage component.

The mechanical-electrical transducer may be in particular a piezoelectric component cyclically and alternately stressed in bending so as to generate within its constituent material electrical charges that are collected at the surface of the component to be used by the self-powering system of the leadless capsule. This piezoelectric component may in particular be a piezoelectric beam clamped at one of its end and coupled to the inertial mass at its other end, which is free.

Such an energy harvester, for powering an implant from the oscillations of a piezoelectric beam, or "PEH" (Piezoelectric Energy Harvester), is described in particular in U.S. Pat. No. 3,456,134 A (Ko) and in above-mentioned WO 2019/001829 A1.

It will be noted that the term "beam" has to be understood in its widest meaning, i.e. an elongated, thin and flat band, it being understood that the shape of this band is not necessarily rectangular nor its thickness constant (as in the description of the particular embodiment that will be given hereinafter). The term "beam", within the meaning of the present invention, hence covers elements that may have a width and/or a thickness that are not constant in the longitudinal direction, as well as, possibly, a deformability going beyond a single degree of freedom in bending.

BRIEF SUMMARY OF THE INVENTION

The starting point of the invention lies in the observation that the mechanical stresses undergone by a leadless capsule, and hence the power delivered by the energy harvester of the latter, may widely vary as a function of the site of implantation and of the situation of the capsule in space once the latter has been anchored to the organ wall.

In particular, with a transducer of the PEH type, whose piezoelectric beam is deformed following the movements of the capsule, the essentially anisotropic character of this beam has for consequence that the amplitude of the deformation—and hence the energy collected at each oscillation—will be minimal if the bending effort exerted to the beam by the inertial mass is parallel to the plane of the beam, whereas it will be maximal when this effort is perpendicular to the plane of the beam.

Now, it is not possible to foresee, at the time of implantation, the dominant direction of the efforts that will be exerted on the capsule. Besides, even if the direction of the capsule were optimum at the time of implantation, it won't be necessarily always the case afterwards, because the external mechanical stresses may vary over time or according to various circumstances, for example the fact that the patient is standing or lying down, is at rest or in effort, etc.

A solution would consist in providing for the energy harvester a configuration with several piezoelectric beams arranged in different directions relative to each other, for example two beams arranged in a cross configuration, or three beams at 120°, so that the mean power collected by the combination of beams is less sensitive to the direction of the capsule.

But such a solution is not concretely conceivable due to the extreme miniaturization of a leadless capsule, which is necessary to allow an endocavitary implantation.

The object of the invention is hence to propose an energy harvesting system of the PEH type, wherein the pendular unit is arranged inside the capsule on a rotationally mobile support, the capsule being provided with a controllable driver for rotating this support so as to search for a direction that maximizes the deformation of the piezoelectric beam, and hence the energy produced by the energy harvester, then holding the pendular unit in this optimum direction.

This driver is preferably an electrically powered and controlled motor, but the invention is not limited to this particular type of driver, and it can also be applied to any suitable rotation means, for example a pre-programmed rotational inertial system or any type of actuator, making it possible to rotationally align the energy harvesting system to a position that maximizes the deformation of the piezoelectric beam.

More precisely, the invention proposes an active medical device of the autonomous implantable capsule type, comprising an elongated capsule body generally extending along a longitudinal axis, the capsule body being provided with an element for its anchoring to a wall of a patient's organ. The capsule body accommodates an electronic unit, an energy harvesting module and an energy storage component for powering the electronic unit, the energy harvesting module comprising: a pendular unit subjected to external stresses applied to the capsule body under the effect of movements of said wall and/or of blood flow rate variations in the surrounding medium, the pendular unit comprising an inertial mass coupled to an elastically deformable beam according to at least one degree of freedom, the beam generally extending along the longitudinal axis of the capsule body between a clamped end and an opposite, free end coupled to the inertial mass; a mechanical-electrical transducer coupled to the beam, for converting into an oscillating electrical signal a mechanical energy produced by the oscillations of the pendular unit; and a power management circuit, adapted to rectify and regulate the oscillating electrical signal to output a stabilized direct voltage or current for powering the electronic unit and/or for charging the energy storage component.

Characteristically of the invention, the energy harvesting module further comprises: a mobile support, integral with the clamped end of the beam and mobile in axial rotation about the longitudinal axis of the capsule body; and a controllable driver, adapted to adjust an angular position in axial rotation of the mobile support with respect to the capsule body.

The beam is preferably a piezoelectric beam forming both said elastically deformable beam and said mechanical-electrical transducer.

The controllable driver is preferably a rotary motor, comprising a rotor integral with the mobile support and a stator integral with the capsule body. The rotary motor is preferably a piezoelectric travelling wave motor.

The rotor and the stator may be concentric annular elements, or disk-shaped flat elements adjacent to each other, with a fixed disk integral with the tubular body and a mobile disk integral with the central mobile part.

The clamped end of the beam is preferably located on a side of the capsule body that is far from the anchoring element, and the free end of the beam is located on a side of the capsule body that is close to the anchoring element.

The controllable driver is advantageously a driver adapted to receive an electrical energy to adjust the angular position of the mobile support with respect to the capsule body, and to hold the adjusted angular position after disappearance of the electrical energy received, without having to apply a holding electrical energy to the driver.

In a preferential embodiment, the energy harvesting module further comprises: power level evaluation circuits, adapted to derive from the oscillating electrical signal a parameter representative of an electrical power produced by the mechanical-electrical transducer; and position servo-control circuits adapted to, in response to the parameter representative of the electrical energy produced, control the controllable driver to adjust the angular position to an optimum angular position that maximizes the electrical power produced by the oscillations of the pendular unit and converted by the mechanical-electrical transducer.

In particular, in this preferential embodiment, the position servo-control circuits comprise a processor and a memory comprising instructions for causing the processor to execute an iterative optimum angular position search process comprising: obtaining a plurality of angular position data and corresponding data of electrical power produced; comparing the successively obtained data of angular position and of electrical power produced; and determining as the optimum angular position an angular position that maximizes the electrical power produced.

The optimum angular position search process may be executed: periodically, at predetermined time intervals; and/or under condition of a minimum level of capacity or voltage of the energy storage component of the device, the minimum level being a level at least sufficient to allow the execution of the optimum angular position search process; and/or when a level of capacity or voltage of the energy storage component of the device becomes lower than a predetermined level threshold.

Moreover, the optimum angular position search process may further comprise memorizing, into a history of the optimum angular positions, the optimum angular position determined at each execution of the search process. In this case, when a level of capacity or voltage of the energy storage component of the device is lower than a predetermined level threshold, the optimum angular position search process determines said optimum angular position in a non-iterative manner by analyzing the history of the optimum angular positions.

In an alternative embodiment, the electronic unit of the device further comprises an emitter/receiver for communicating with a programmer external to the device, and the position servo-control circuits comprises a processor and a memory comprising instructions to cause the processor to execute a optimum angular position search process, comprising: obtaining a plurality of angular position data and corresponding data of electrical power produced; sending to the external programmer the data of angular position and of electrical power produced; and receiving from the programmer the optimum angular position that maximizes the electrical power produced.

BRIEF DESCRIPTION OF THE DRAWINGS

The foregoing and other objects, aspects and advantages of the invention will be better understood from the following detailed description of a preferred embodiment of the invention with reference to the appended drawings, in which the same numerals refer to identical or functionally similar features over the different figures.

DETAILED DESCRIPTION OF A PREFERRED EMBODIMENT OF THE INVENTION

An exemplary embodiment of the device of the invention will now be described.

As regards the software aspects thereof, the invention may be implemented by a suitable programming of the leadless capsule control software. The adaptation of these devices to implement the invention is within the reach of the one skilled in the art, and it won't be described in detail. In particular, it will be possible to adapt the software programs stored in memory and executed, and to use them to implement the functions of the invention that will be described hereinafter. The method of the invention implements software means, using suitable algorithms executed by a microcontroller or a digital signal processor. For the sake of clarity, the various processings applied will be decomposed and schematized by a number of distinct modules or functional blocks and/or interconnected circuits, but this representation is however only illustrative, these functions or circuits having common elements and corresponding in practice to a plurality of functions globally executed by a same software program.

Figure 1:
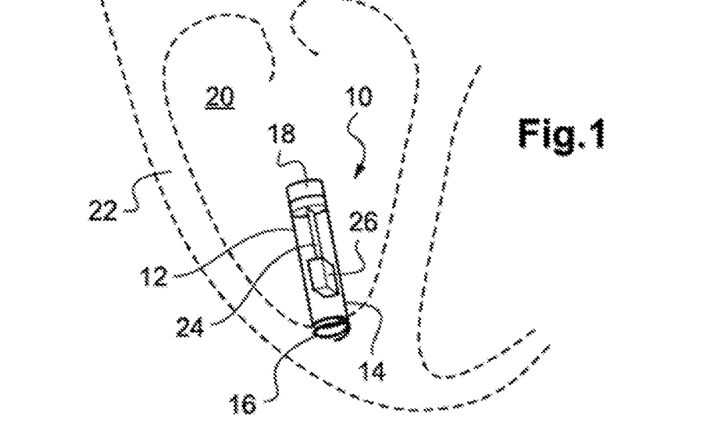
FIG. 1 illustrates a medical device of the leadless capsule type in its environment, implanted in the bottom of the right ventricle of a patient.

FIG. 1 shows a device of the leadless capsule type 10 in a cardiac stimulation application.

The capsule 10 is made in the external form of an implant with an elongated cylindrical tubular envelope 12 enclosing the various electronic and power supply circuits of the capsule, as well as a pendular unit energy harvester. The typical dimensions of such a capsule are a diameter of the order of 6 mm for a length of about 25-40 mm.

The tubular envelope 12 has, at its front (distal) end 14, a protruding anchoring element, for example an helical screw 16, to hold the capsule on the implantation side. Other anchoring systems can be used, and do modify in any way the implementation of the present invention. The opposite (proximal) end 18 of the capsule 10 is a free end, which is only provided with means for the link to a guide-catheter (not shown) or another implantation accessory usable at the time of implantation or explanation of the capsule and then disconnected from the latter.

In the example illustrated in FIG. 1, the leadless capsule 10 is an endocavitary implant implanted into a cavity 20 of the myocardium 22, for example at the apex of the right ventricle. As a variant, still in a cardiac stimulation application, the capsule may also be implanted on the interventricular septum or on an atrial wall, or also be an epicardial capsule placed on an external region of the myocardium, wherein these different implantation modes do not modify in any way the implementation of the present invention. To perform the detection/stimulation functions, an electrode (not shown) in contact with the cardiac tissue at the implantation site collects cardiac depolarization potentials and/or applies stimulation pulses. In certain embodiments, the function of this electrode may be provided by the anchoring screw 16, which is then an active screw, electrically conductive and connected to the detection/stimulation circuit of the capsule.

The leadless capsule 10 is moreover provided with an energy harvesting module comprising an inertial pendular unit that oscillates, inside the capsule, following the various external stresses to which the capsule is subjected. These stresses may in particular result from: the movements of the wall to which the capsule is anchored, which are transmitted to the tubular body 12 by the anchoring screw 16; and/or the blood flow rate variations in the medium surrounding the capsule, which produce oscillations of the tubular body 12 at the rhythm of the heartbeats; and/or the various vibrations transmitted by the cardiac tissues.

The pendular unit may in particular be consisted by a piezoelectric beam 24 clamped at one of its ends and whose opposite, free end is coupled to a mobile inertial mass 26.

The piezoelectric beam 24 is an elastically deformable flexible beam that constitutes, with the inertial mass 26, a pendular system of the mass-spring type. Due to its inertia, the mass 26 subjects the beam 24 to a deformation of the vibratory type on either side of a neutral or non-deformed position corresponding to a stable rest position in the absence of any stress.

Actually, this unit may be equated, as for its mechanical behavior, to a structure of the "clamped/free beam" type, having a natural frequency of oscillation, which is herein the frequency at which the mass-spring system oscillates. It will be noted that this natural frequency of oscillation, typically of the order of a few tens of hertz, is noticeably higher than the frequency of the external cyclic stresses that correspond to the frequency of the heartbeats (at most a few hertz). Hence, at each heart contraction, the inertial mass (or other functionally similar mechanical component) will be stressed with a more or less high amplitude, then the pendular system will oscillate several times with decreasing amplitudes (bounces characteristic of a damped periodic oscillation), and will finally stabilize up to the following heartbeat, where the stress/oscillation cycle will be comparably repeated.

The piezoelectric beam 24 further performs a function of mechanical-electrical transducer making it possible to convert into electrical charges the mechanical bending stress that is applied to it. These charges are collected by electrodes at the surface of the beam to produce an electrical signal that, after rectification, stabilization and filtering will power the various electronic circuits of the capsule.

The beam is advantageously a beam of the bimorphous type, i.e. capable of generating energy on its two faces when subjected to a deformation. Theses transduction properties are typical of a piezoelectric material, such as the PZT ceramics or the mono-crystals of the PMN-PT, barium titanate or lithium niobate type.

Figure 2:
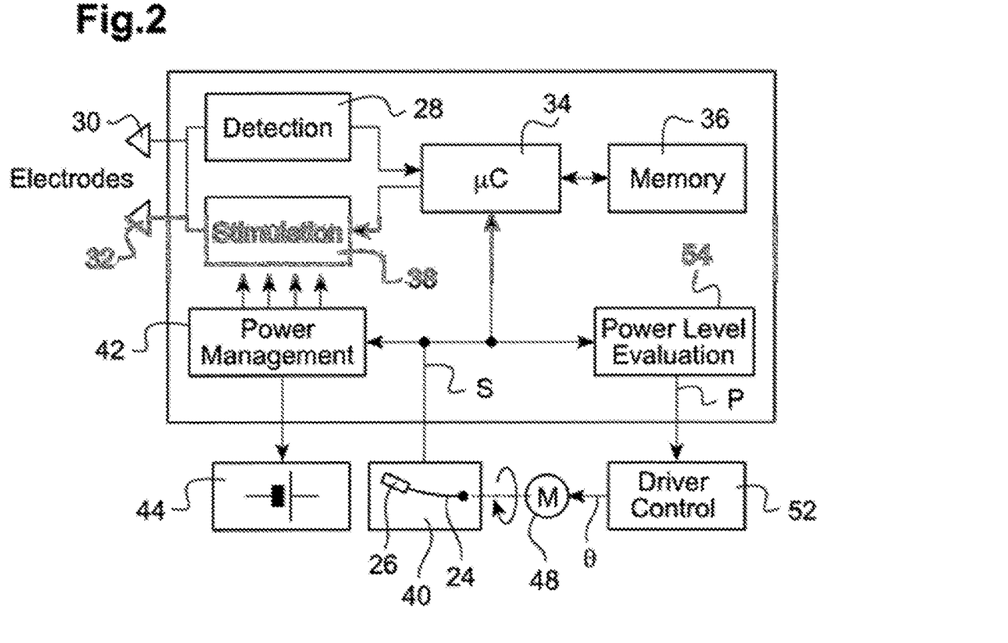
FIG. 2 schematically shows the main functional elements constitutive of the leadless capsule.

FIG. 2 is a synoptic of the various electric and electronic circuits integrated to the leadless capsule, shown as functional blocks. These circuits are advantageously made as an ASIC or a combination of ASICs.

The block 28 represents a heart depolarization wave detection circuit, connected to a cathode electrode 30 in contact with the cardiac tissue and to an associated anode electrode 32, for example an annular electrode formed on the tubular body of the capsule. This detection block 28 comprises filters and means for the analog and/or digital processing of the collected signal. The so-processed signal is applied to the input of a microcalculator 34 associated with a memory 36. The electronic unit also includes a stimulation circuit 38 operating under the control of the microcalculator 34 to deliver as needed myocardium stimulation pulses to the system of electrodes 18, 20.

An energy harvesting circuit 40 is moreover provided, consisted by the pendular unit formed by the piezoelectric beam 24 and the inertial mass 30 described hereinabove with reference to FIG. 1. As the piezoelectric beam 24 also performs a function of mechanical-electrical transducer, it converts into electrical charges the mechanical stresses undergone and produces a variable electrical signal S that is delivered to an energy management circuit 42. This circuit 42 rectifies and regulates the signal S so as to output a stabilized direct tension or current for powering the electronic unit and charging an integrated energy storage component 44, for example a rechargeable battery or a high-performance capacitor powering the electronic unit.

Figure 3:
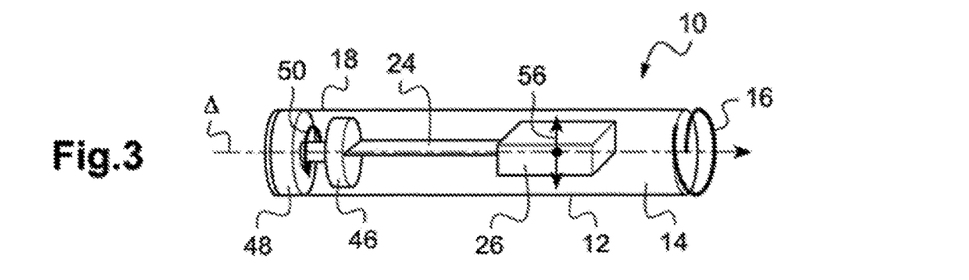
FIG. 3 is a perspective schematic view showing the mechanical configuration of the main elements of the energy harvester of the leadless capsule of the invention.

FIG. 3 schematically illustrates the mechanical configuration of the main elements of the energy harvester according to the invention.

The basic principle of the invention consists in rotating in a controlled manner the beam 24 about its longitudinal axis 4, which is also the longitudinal axis of the tubular body 12 of the capsule 10.

For that purpose, the clamped end of the beam 24 is mounted on a support 46 mobile in rotation about the axis 4. A driver 48 allows rotating the support 46 about the axis Δ (arrow 50) and hence adjusting the angular position of the pendular beam 24-mass 26 unit (the beam 24 and the mass 26 remaining integral with each other).

The driver 48 is controlled by a circuit 52 (FIG. 2) servo-controlled by a circuit 54 for evaluating the level of the power delivered by the energy harvesting module 40.

The unit formed by the driver 48, the energy harvesting module 40 and the circuits 52 and 54 forms a servo-control loop for automatically adjusting the angular position θ of the pendular beam 24-mass 26 unit to an optimum position that maximizes the power P delivered.

Indeed, the beam 24 being flat, its bending response is anisotropic according to the different directions about the axis Δ (radial directions), with a maximum sensitivity to the forces that are perpendicular to the plane of the beam surface, and a minimum sensitivity to the forces that are directed in this same plane.

Another anisotropy with respect to Δ exists, which is that of the external stresses applied to the tubular body 12 of the capsule 10, and consequently, of the effort (arrow 56) applied to the free end of the beam 24 by the inertial mass 26.

It has been observed that, in the frequency domain, this anisotropy is particularly marked about the resonance frequency of the beam 24-mass 26, typically about 20 Hz (as indicated hereinabove, the oscillation frequency of the pendular unit is significantly higher than the frequency of the heartbeats, which is of the order of 1-2 Hz).

In other words, on the one hand, the beam has a privileged bending direction that is perpendicular to the plane of its surface, and on the other hand, the bending stress it may receive at its free end has a dominant direction depending on multiple non-predictable factors, such as the axial direction of the capsule at the end of screwing to the implantation site, the dynamics of the cardiac wall movement, the dynamics of the blood flow in which soaks the capsule, the gravity direction (itself function of the patient's position: standing, lying on the back, on the side . . . ), etc.

The aim is to make these two privileged directions coincide with each other by a suitable rotation of the mobile support 46 inside the tubular body 12 of the capsule, to search for the angular position about the axis 4 that will maximize the effort applied at the free end of the beam 24, hence the bending deformation of the latter, and consequently the electrical charge produced by the mechanical-electrical transduction and finally the electrical power P delivered by the energy harvester 40.

Figure 4A:
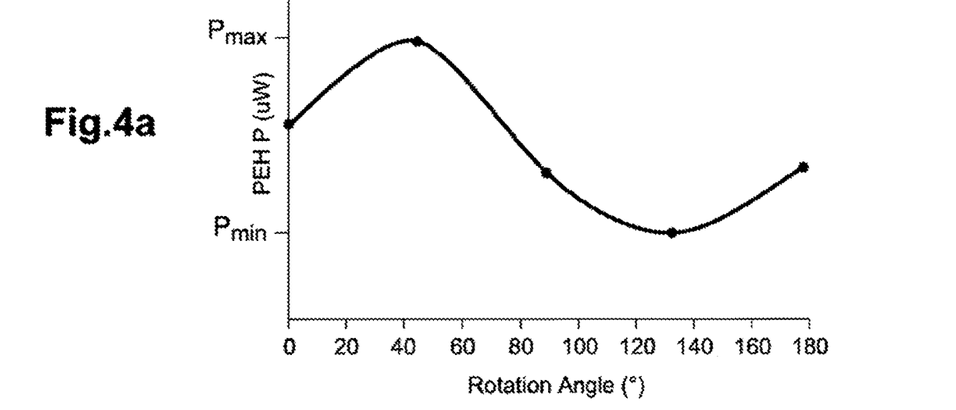
FIGS. 4a and 4b are examples of records of the output power produced by the energy harvester as a function of the direction angle of the pendular unit, for two leadless devices implanted in different organisms.
Figure 4B:
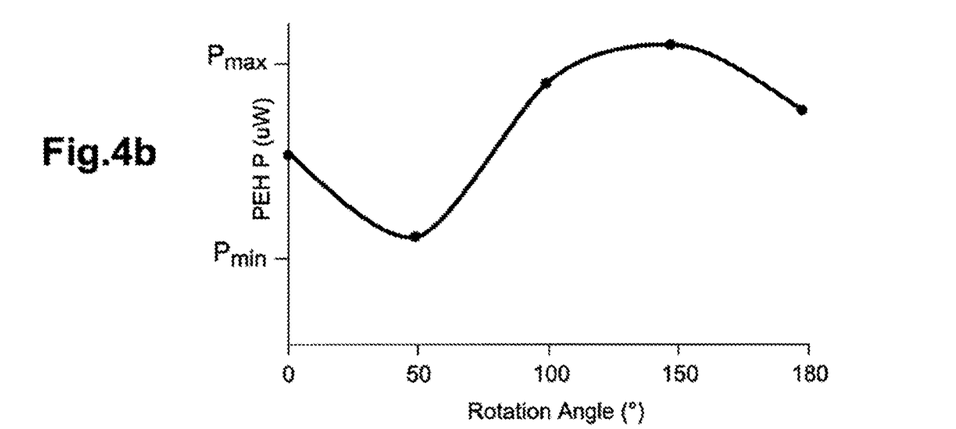

FIGS. 4a and 4b illustrate, for two implantations of a same leadless capsule in different organisms, records of the output power P delivered by the energy harvester 40 as a function of the angle θ corresponding to the direction of the pendular beam 24-mass 26 unit.

It can be observed a very significant difference between the respective powers delivered in the optimum angular configuration ($P_{max}$) and the less favorable configuration ($P_{min}$), with typically a $P_{max}:P_{min}$ ratio of the order of 3:1.

The gain in produced power that may be obtained by a controlled adjustment of the angular position of the beam may hence be very high. It can also be observed on these records that the angular difference between the most favorable position and the less favorable one is of about 90° in one direction or the other.

Figure 5A:
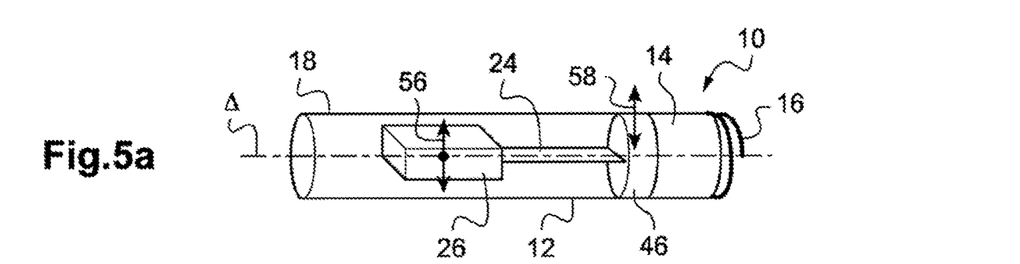
FIGS. 5a and 5b are homologous to FIG. 3 and illustrate the two possible configurations according to which the pendular unit can be arranged inside the leadless capsule.
Figure 5B:
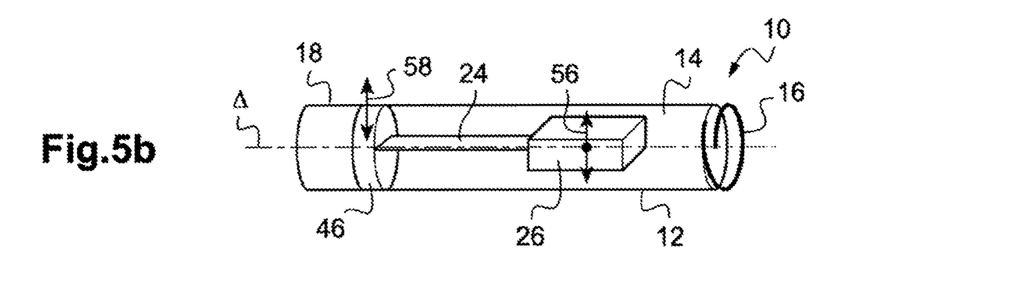

FIGS. 5a and 5b illustrate the two possible configurations according to which the pendular unit may be arranged inside the leadless capsule.

In the configuration of FIG. 5a, the support 46 carrying the clamped end of the beam 24 is located on the side of the distal end 14 of the tubular body 12, whereas, in the configuration of FIG. 5b, the support 46 is, conversely, located on the side of the proximal end 18 of the tubular body 12.

The configuration of FIG. 5a favors, for the driving of the inertial mass 26, the stresses coming from movements of the cardiac wall at the anchoring point 16 on the distal side 14 of the capsule, whereas the configuration of FIG. 5b favors the stresses coming from the variations of the blood flow rate acting on the free end on the proximal side 18 of the capsule 10.

In either case, the power delivered by the energy harvester after mechanical-electrical conversion will be function of the acceleration applied (arrow 58) at the clamped end of the beam 24, at the origin of the oscillations of the inertial beam 24-mass 26 unit. Concretely, it has however been observed that the configuration of FIG. 5b (clamped end of the beam on the side of the capsule free end) produces a greater amplitude of oscillation of the inertial unit and hence leads to a better efficiency of the energy harvesting module.

Choosing one or the other configuration does not modify in any way the implementation of the present invention as regards the search for the angular direction (about the axis 4) that maximizes the power delivered by the pendular beam 24-mass 26 unit inside the tubular body 12, whatever the way this pendular unit is mounted, in one direction or the other, inside the tubular body.

Figure 6:
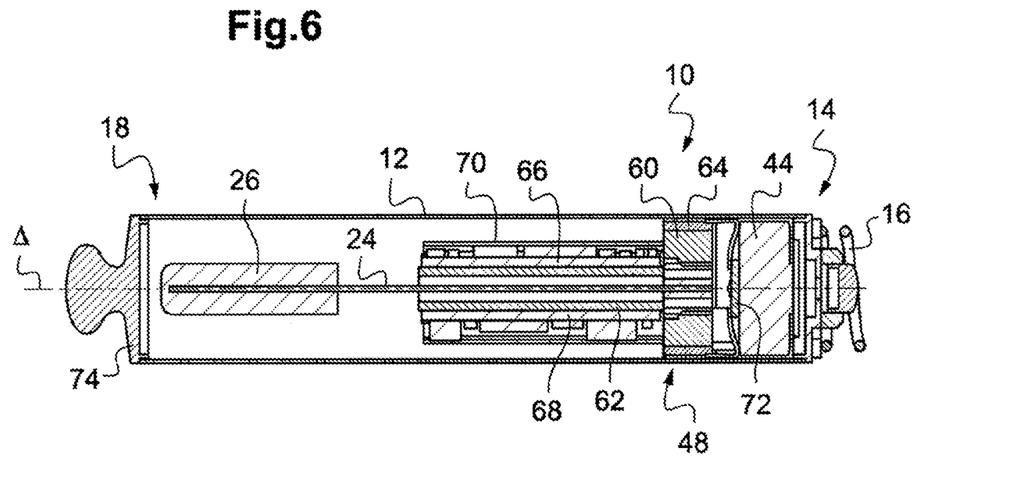
FIG. 6 is a detailed longitudinal cross-sectional view of a leadless capsule according to the invention, showing the different elements of which it is composed.
Figure 7:
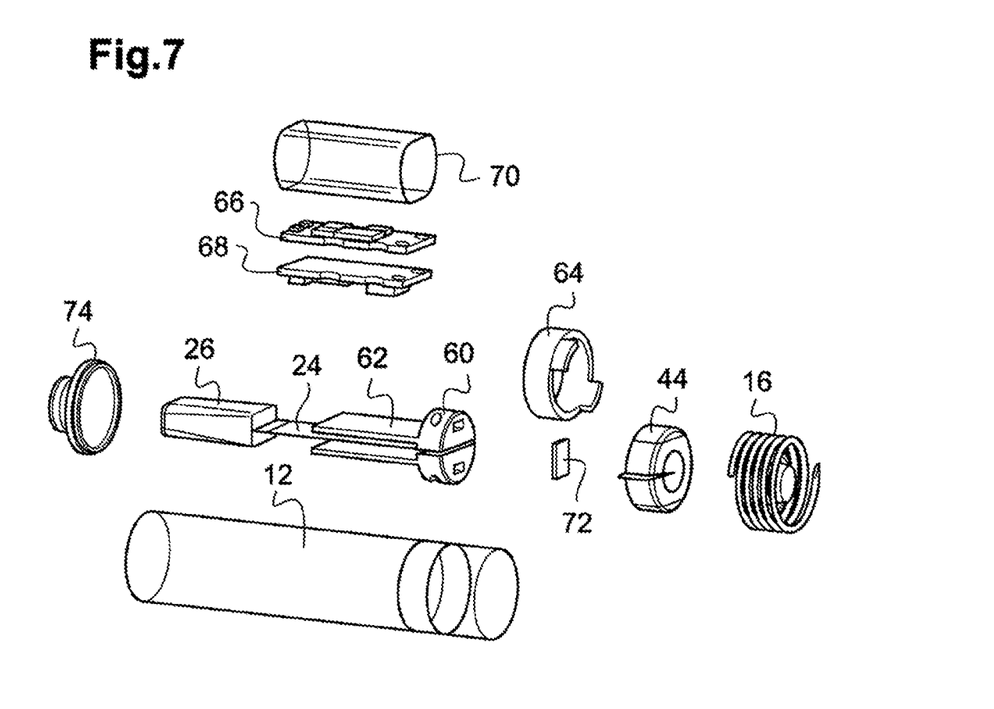
FIG. 7 is an exploded perspective view showing separately the different subassemblies constitutive of the capsule of FIG. 6.

FIGS. 6 and 7 illustrate a detail example of implementation of a leadless capsule according to the invention, in longitudinal cross-sectional view showing the different elements of the capsule assembled together, and in exploded view showing separately the different subassemblies gathering these same elements, respectively. The description of this example is however not limitative and many variants may be contemplated without departing from the scope of the invention.

In this example, the driver 48 is a rotary motor comprising, on the one hand, a rotor 60 integral with a mobile part 62 into which is clamped the beam 24, and on the other hand, a stator 64 integral with the tubular body 12 of the capsule 10.

The rotor 60 and the stator 64 may be, as illustrated, concentric annular elements. As a variant, they may also be made as two disk-shaped flat elements adjacent to each other, with a fixed disk integral with the tubular body 12 and a mobile disk integral with the central mobile part 62.

The unitary assembly consisted by the central mobile part 62, the beam 24 and the inertial mass 26 forms a mobile assembly able to rotate axially about the axis Δ with respect to the tubular body 12 of the capsule 10. The stator 64 is integral with the tubular body 12 and the elements supported by the latter, such as in particular the anchoring screw 16.

Moreover, to optimize at best the space inside the capsule and to clear the central space for the beam 24, the mobile part 62 has two support faces arranged symmetrically on either side of the beam and accommodating two printed circuit boards (PCBs) 66, 68. On these PCBs are mounted the various electronic components corresponding to the blocks 28, 34, 36, 38, 42 and 54 of FIG. 2, the whole circuits being surrounded by a sheath 70 protecting them inside the tubular body 12 and hermetically enclosed in the tubular body 12 by a closing cap 74 mounted at the proximal end 18.

For the control electronics of the driver 48, it is preferably provided a PCB 72 distinct from the PCBs 66 and 68. Indeed, the control of the motor uses voltages and currents far higher than those of the electronic components of the boards 66 and 68. This PCB 72 is for example placed near the stator 64, and is connected to the rotor 60 through flexible conductors.

In a preferential embodiment of the invention, the driver 48 comprising the rotor 60 and the stator 64 advantageously implements a technology of piezoelectric travelling wave motor, such technology having many advantages in the particular application contemplated herein, in particular:

compliance with the very strict requirements of integration into an implantable leadless capsule (small volume, robustness, reliability over a very long duration);

manufacturing requiring only a small quantity of piezoelectric material for the motor;

high torque and low speed of rotation, allowing direct driving without reduction gear;

very short response time, of the order of a few milliseconds;

very low sound level (important characteristic in the case of an implant, whose operation must not disturb the patient);

"MRI-Safe", i.e. insensitivity to intense magnetic fields undergone during examinations using MRI devices (unlike electromagnetic motors, which may be damaged by such intense magnetic fields); and "Self-retention", i.e., in the absence of power supply applied to the motor, the angular position of the rotor with respect to the stator is maintained without energy consumption, by a friction force and a pre-stress at rest inherent to the technology of the piezoelectric travelling wave motors.

These motors are per se well known, e.g. from U.S. Pat. No. 4,019,073 A, 4,339,682 A, 4,484,099 A, 4,562,373 A, 4,739,212 A, or 7,579,750 A.

In the particular case of the present invention, the piezoelectric travelling wave motor of the driver 48 may be driven in particular with the following parameters:

amplitude of rotation ±90° (or 0-180°);

angular adjustment by pitches of about 5°; and speed of rotation of the order of 0.1°/s, compatible with time needed for collecting successive samples of power produced and processing corresponding data (see hereinafter).

Figure 8:
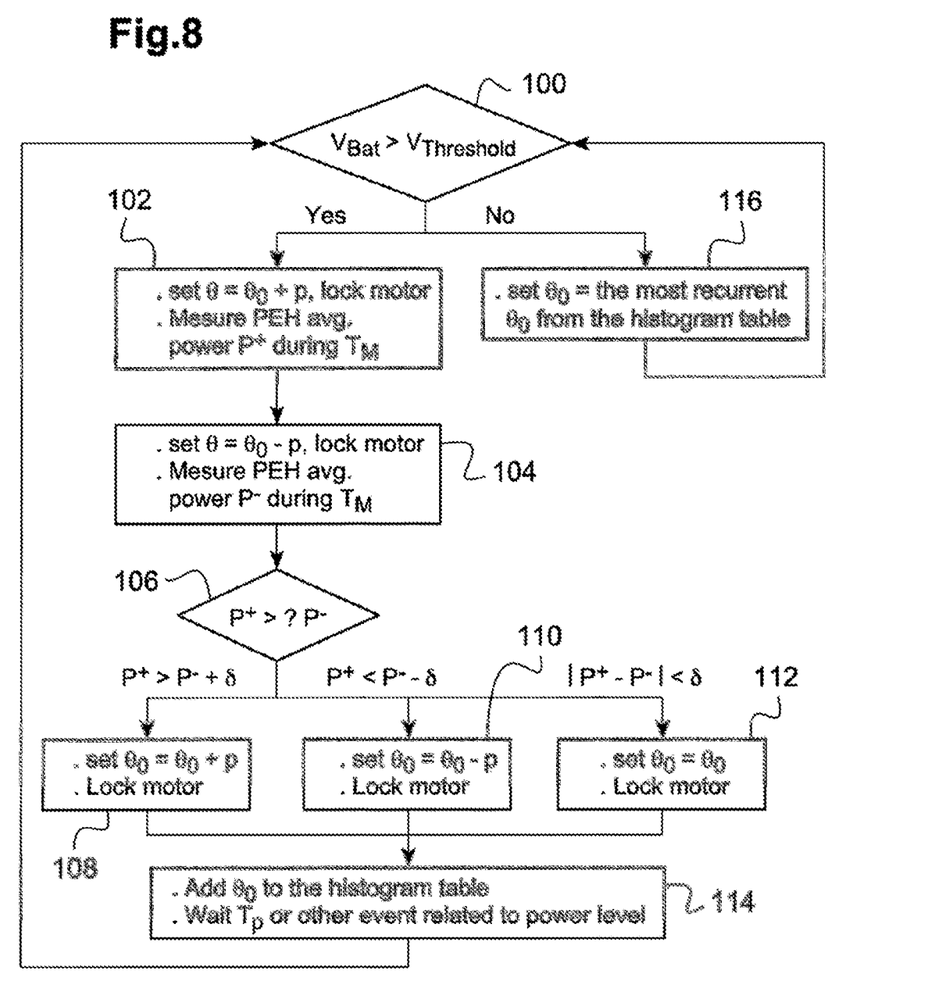
FIG. 8 is a flow diagram showing the successive steps of an example of process for searching the optimum direction of the pendular unit.
Figure 9:
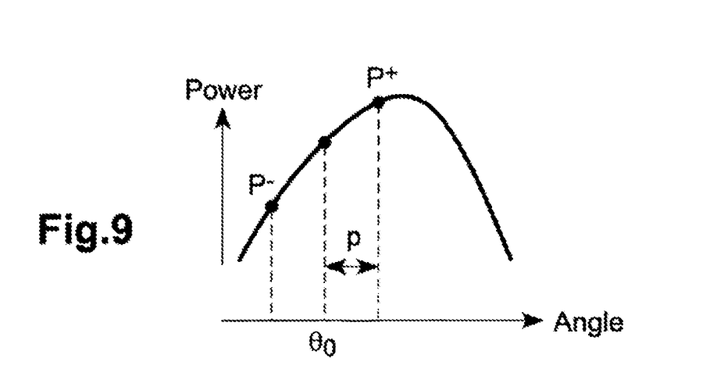
FIG. 9 is a curve giving the output level delivered by the energy harvester as a function of the direction angle of the pendular unit, and the way to travel through the steps of FIG. 8.

FIGS. 8 and 9 set forth the successive steps of a process for finding the optimum direction of the pendular unit that will provide the highest power level.

It will be noted that the sequence of steps that will be described is given only by way of non-limitative example, and a very large number of variations may be contemplated, which do not modify in any way the implementation of the present invention.

In particular, in the example of FIG. 8, all the calculations of the process are operated inside the capsule (by the circuits of blocks 52 and 54 of FIG. 2). As a variant, a part of these calculations may however be operated by a device that is external to the device, for example a programmer controlled by a practitioner, interfaced by telemetry to the capsule on the occasion of a follow-up consultation of the patient. In this latter case, it is sufficient that the capsule collects the data of angular position θ and of corresponding power P produced, transmits these data elements to the programmer (or to any other device external to the capsule) by telemetry, then receives from the programmer the result of the analysis of these data elements, as an indication of the optimum angular position $\theta_o$ that maximizes the electric power produced. The pendular unit will then be redirected based on this indication.

In the process illustrated in FIG. 8, the device first makes sure (test 100) that the voltage $V_{Bat}$ across the battery is higher than a threshold voltage $V_{Threshold}$, i.e. it remains enough energy available stored in the capsule battery to supply the motor during the whole duration of a full process of iterative search.

If such is the case, the device rotates the rotor (block 102) by a pitch p in one direction with respect to the current position $\theta_o$, which was the preceding optimum position, and locks the motor in this new position (a locking that results, with a piezoelectric travelling wave motor, from the simple stop of supply of the motor). The device then measures the mean power P+ produced by the energy harvester during a predetermined duration $T_M$ according to the change of angle.

At the following step (block 104), the device supplies the motor again to displace the rotor to an angular position $\theta=\theta_o-p$, then measures the power P− produced at this new position during the same duration $T_M$ as at the preceding step.

The device then compares (test 106) the two power values P+ and P− obtained:
  if P+>P− (within a minimum difference δ), then the device adjusts the pendular unit to the position $\theta_o+p$ (block 108);
  if P+<P− (within the minimum difference δ), then the device adjusts the pendular unit to the value $\theta_o-p$ (block 110);
  if the measured values P+ and P− are close to each other (lower than δ), then the device considers that it is not necessary to modify the initial angular position $\theta_o$ and keeps the latter for the following (block 112).

The new value $\theta_o$ is then stored (block 114) and the device waits for the reiteration of the search process that has just been described (steps 100 to 112), the reiteration being triggered, for example, by:
  timeout of a fixed delay $T_p$; and/or
  occurrence of a specific event revealing or having an incidence on the level of electric power produced (for example, when the battery level and/or the voltage delivered by the energy harvester become lower than a predetermined threshold, which means that the charge of the battery is not sufficient); and/or
  durable change of a state of the patient or of his/her position in space (standing, lying on the back, on the side . . . ).

If, at step 100, the device determines that the voltage $V_{Bat}$ across the battery, representative of the charge level of the latter, is lower than a threshold voltage $V_{Threshold}$, then (block 116) the device refrains from triggering a search involving the actuation of the motor and hence the consumption of a corresponding quantity of energy.

In this case, the optimum position $\theta_o$ is determined for example from a history of all the optimum positions $\theta_o$ that had been previously found and memorized at step 114 of each iteration of the process. The device selects for example as an optimum angular position $\theta_o$ the position that comes back the most often in the history and adjusts the pendular unit to this value.

The invention claimed is:

1. An active medical device of the autonomous implantable capsule type, comprising an elongated capsule body generally extending along a longitudinal axis, the capsule body being provided with an element for its anchoring to a wall of a patient's organ,
  wherein the capsule body accommodates an electronic unit, an energy harvesting module and an energy storage component for powering the electronic unit,
  wherein the energy harvesting module comprises:
    a pendular unit subjected to external stresses applied to the capsule body under the effect of movements of said wall and/or of blood flow rate variations in the surrounding medium, the pendular unit comprising an inertial mass coupled to an elastically deformable beam according to at least one degree of freedom, the beam generally extending along the longitudinal axis of the capsule body between a clamped end and an opposite, free end coupled to the inertial mass;
    a mechanical-electrical transducer coupled to the beam, for converting into an oscillating electrical signal a mechanical energy produced by the oscillations of the pendular unit; and
    a power management circuit, adapted to rectify and regulate the oscillating electrical signal to output a stabilized direct voltage or current for powering the electronic unit and/or for charging the energy storage component,
  wherein the energy harvesting module further comprises:
    a mobile support, integral with the clamped end of the beam and mobile in axial rotation about the longitudinal axis of the capsule body; and
    a controllable driver, adapted to adjust an angular position in axial rotation of the mobile support with respect to the capsule body.

2. The device of claim 1, wherein the beam is a piezoelectric beam forming both said elastically deformable beam and said mechanical-electrical transducer.

3. The device of claim 1, wherein the controllable driver is a rotary motor, comprising a rotor integral with the mobile support and a stator integral with the capsule body.

4. The device of claim 3, wherein the rotor and the stator are concentric annular elements.

5. The device of claim 3, wherein the rotor and the stator are disk-shaped flat elements adjacent to each other, with a fixed disk integral with the tubular body and a mobile disk integral with the central mobile part.

6. The device of claim 3, wherein the rotary motor is a piezoelectric travelling wave motor.

7. The device of claim 1, wherein the clamped end of the beam is located on a side of the capsule body that is far from the anchoring element, and the free end of the beam is located on a side of the capsule body that is close to the anchoring element.

8. The device of claim 1, wherein the controllable driver is a driver adapted to:
  receive an electrical energy to adjust the angular position of the mobile support with respect to the capsule body, and
  hold the adjusted angular position after disappearance of the electrical energy received, without having to apply a holding electrical energy to the driver.

9. The device of claim 1, wherein the energy harvesting module further comprises:
  power level evaluation circuits, adapted to derive from the oscillating electrical signal a parameter representative of an electrical power produced by the mechanical-electrical transducer; and
  position servo-control circuits adapted to, in response to the parameter representative of the electrical energy produced, control the controllable driver to adjust the angular position to an optimum angular position that maximizes the electrical power produced by the oscillations of the pendular unit and converted by the mechanical-electrical transducer.

10. The device of claim 9, wherein the position servo-control circuits comprise a processor and a memory comprising instructions for causing the processor to execute an iterative optimum angular position search process comprising:
   obtaining a plurality of angular position data and corresponding data of electrical power produced;
   comparing the successively obtained data of angular position and of electrical power produced; and
   determining as the optimum angular position an angular position that maximizes the electrical power produced.

11. The device of claim 10, wherein the optimum angular position search process is executed periodically, at predetermined time intervals.

12. The device of claim 10, wherein the optimum angular position search process is executed under condition of a minimum level of capacity or voltage of the energy storage component of the device, the minimum level being a level at least sufficient to allow the execution of the optimum angular position search process.

13. The device of claim 10, wherein the optimum angular position search process is executed when a level of capacity or voltage of the energy storage component of the device becomes lower than a predetermined level threshold.

14. The device of claim 10, wherein the optimum angular position search process further comprises memorizing, into a history of the optimum angular positions, the optimum angular position determined at each execution of the search process, and wherein when a level of capacity or voltage of the energy storage component of the device is lower than a predetermined level threshold, the optimum angular position search process determines said optimum angular position in a non-iterative manner by analyzing the history of the optimum angular positions.

15. The device of claim 9,
   wherein the electronic unit of the device further comprises an emitter/receiver for communicating with a programmer external to the device,
   and wherein the position servo-control circuits comprises a processor and a memory comprising instructions to cause the processor to execute a optimum angular position search process, comprising:
      obtaining a plurality of angular position data and corresponding data of electrical power produced;
      sending to the external programmer the data of angular position and of electrical power produced; and
      receiving from the programmer the optimum angular position that maximizes the electrical power produced.

* * * * *